United States Patent [19]

Carlson et al.

[11] 4,376,124
[45] Mar. 8, 1983

[54] METHOD FOR MODULATING THE IMMUNE RESPONSE WITH DIBENZOCYCLOHEPTENYLIDENES

[75] Inventors: Richard P. Carlson, Lansdale; Richard L. Fenichel, Plymouth Meeting; Alan J. Lewis, Audubon; Milton Wolf, West Chester, all of Pa.

[73] Assignee: American Home Products Corporation, New York, N.Y.

[21] Appl. No.: 356,005

[22] Filed: Mar. 8, 1982

[51] Int. Cl.³ .................. A61K 31/19; A61K 31/235
[52] U.S. Cl. ..................................... 424/308; 424/317
[58] Field of Search ............................... 424/308, 317

[56] References Cited

U.S. PATENT DOCUMENTS 4,267,192 5/1981 Wolf ................................. 424/308

*Primary Examiner*—Stanley J. Friedman
*Attorney, Agent, or Firm*—George Tarnowski

[57] ABSTRACT

A method of modulating the immune response in mammals by administering thereto compounds having the general formula:

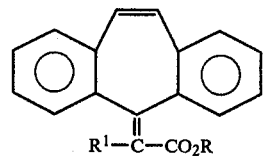

where R is hydrogen or alkyl of 1–4 carbon atoms, $R^1$ is hydrogen or an alkyl of 1–4 carbon atoms and pharmaceutically acceptable salts thereof.

4 Claims, No Drawings

METHOD FOR MODULATING THE IMMUNE RESPONSE WITH DIBENZOCYCLOHEPTENYLIDENES

This invention relates to a method of modulating the immune response in mammals by the administration of dibenzocycloheptenylidenes.

In U.S. Pat. No. 4,267,192, there was disclosed a method of treating inflammation in mammals by the administration of compounds having the formula

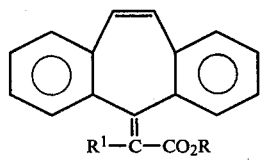

where R is hydrogen or an alkyl group of 1–4 carbon atoms, $R^1$ is hydrogen or an alkyl group of 1–4 carbon atoms, and pharmaceutically acceptable salts thereof. It has now been determined that these compounds also possess significant immunomodulating activity towards both the humoral and cellular immune response.

While the currently available nonsteroidal anti-inflammatory drugs, such as indomethacin, naproxen, sulindac, flurbiprofen, aspirin and piroxicam, are able in some measure to help alleviate the debilitating effects of the inflammatory process itself they do not modify the underlying autoimmune processes which are thought to be directly responsible for eliciting the inflammatory processes in such diseases as rheumatoid arthritis. The failure to check the immunologic imbalance permits the formulation and deposition of immune complexes, and leaves hyperactivity of the cellular immune response to continue uncontrolled. This perpetuation of the inflammatory response leads to the gradual destruction of the affected joints. Accordingly, the elucidation and development of drugs capable of modifying the underlying immunological causes of the inflammatory process are of paramount importance in attempting to deal with the course of such inflammatory diseases as rheumatoid arthritis, systemic lupus erythematosus and so forth.

As indicated earlier, it has now been discovered that the compounds disclosed in U.S. Pat. No. 4,267,192, in addition to their significant anti-inflammatory activity, also possess significant immunomodulatory properties, which makes these compounds useful in treating diseases and disorders in which modulation of the immune response is indicated. Thus, the compounds can be used in treating inflammatory autoimmune diseases such as systemic lupus erythematosus. It is significant to note that the nonsteroidal anti-inflammatory drugs (NSAIDs), which are currently used in the therapy of such inflammatory diseases as rheumatoid arthritis do not have any significant immuno-modulatory properties, so that the compounds used in the present invention do not act in the same manner as the conventional NSAIDs. Indeed, it is postulated that the compounds of the present invention act through a hitherto unknown and undefined mechanism.

The compounds of the invention can be prepared according to conventional general methods, for example by the Wittig-Horner reaction sequence described by C. D. Bergmann and A. Solomonovici, *Synthesis* 1970, pages 183–188. In the latter case, 5H-dibenzo[a,d]cyclohepten-5-one is reacted with a trialkyl phosphonoalkanoate and sodium hydride in an organic solvent, the resulting alkyl 5H-dibenzo[a,d]cyclohepten-5-ylidene alkanoate is saponified with a base and then recovered as a salt or the free acid. The esters can be prepared either directly by the method just described or by esterifying the free acid. Moreover, the compounds can be prepared from 5H-dibenzo[a,d]cyclohepten-5-one via the Reformatsky reaction or via the modified Reformatsky reaction using lithium salts of α-lithiocarboxylic acids. The starting 5H-dibenzo[a,d]cyclohepten-5-one is a commercially available compound or it can be prepared according to W. Treibs and H. J. Klinkhammer, *Chem. Ber.* 84, 671 (1951).

The pharmaceutically acceptable salts of the free acid include the sodium, potassium, ammonium, and lower alkylamine salts, which are prepared and isolated by conventional methods.

The compounds as used in the method of invention are immunomodulatory agents having significant activity in the treatment of diseases and disorders requiring modulation of the immune response. In this regard, the compounds can be used in the treatment of autoimmune diseases, such as systemic lupus erythematosus, autoimmune hemolytic anemia, rheumatoid arthritis, ankylosing spondylitis, Reiter's Syndrome and so forth, as well as in disorders closely associated with autoimmunity, such as for example multiple sclerosis. Moreover, since the compounds of the invention do not act by stimulating the steroids naturally occurring in mammals, nor do these compounds produce gastric secretion, even at high doses, and since these compounds additionally have a lack of general pharmacologic activity, they are of particular use in the long-term treatment of chronic immunologically inspired disorders, which, for example, are present in systemic lupus erythematosus and other connective tissue disorders.

When the compounds of the invention are employed as immunomodulatory agents, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth methyl cellulose, sodium carboxymethyl cellulose, low melting wax, cocoa butter, and the like. Diluents, flavoring agents, solubilizers, lubricants, suspending agents, binders, tablet-disintegrating agents and the like may be employed. The compound may be encapsulated with or without other carriers. In all cases the proportion of active ingredients in said compositions both solid and liquid will be at least sufficient to impart immunomodulatory activity thereto on oral administration. The compounds may also be injected parenterally, in which case they are used in the form of a sterile solution containing other solutes, for example, enough saline or glucose to make the solution isotonic.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration level that will generally afford effective results without causing any harmful or deleterious side effects. With large animals (about 70 kg. body weight), for oral administration the dose is from about 10 milligrams to about 200 milligrams per day either as a single unit dose, or if desired, the dosage may be divided into convenient subunits administered at convenient times throughout the day, or on a weekly or bi-weekly basis.

The immunomodulatory effects of the compounds of the invention may be demonstrated by standard pharmacological procedures, which are described more fully in the examples given hereinafter.

These procedures illustrate the ability of the compounds of the invention to exert immunomodulatory effect as measured in the murine methylated bovine serum albumin (MBSA) assay, in the tuberculin-induced delayed hypersensitivity test in guinea pigs, in the Jerne plaque assay, in the experimental allergic encephalomyelitis test in rats, and finally the ability of the compounds to affect T and B lymphocyte proliferation in the presence of suboptimal as well as higher concentrations of the mitogen Concanavalin A and of lipopolysaccharide.

EXAMPLE 1

(5H-Dibenzo[a,d]cyclohepten-5-ylidene)acetic acid

A mixture of 65.24 g. (0.291 moles) triethyl phosphonoacetate and 13.967 g. of 50% in oil (0.291 mole) sodium hydride in 750 ml. dry dimethyl sulfoxide is stirred overnight at ambient temperature in a nitrogen atmosphere. 60.00 g. (0.291 moles) 5H-dibenzo[a,d]cyclohepten-5-one is added to the mixture and after stirring at ambient temperature for one hour, the mixture is heated, with stirring, at 100±1° C. for thirty hours. The dimethyl sulfoxide is distilled in vacuo and the oily residue refluxed with a solution of sodium hydroxide in 50% ethanol (400 mL of 12.5%) for sixteen and one-half hours. The solvent is distilled in vacuo and the residue diluted with 100 mL water. The mixture is extracted successively with 200 mL. of 1:1 tolueneheptane and 200 mL. toluene. The dark aqueous layer is decolorized with Darco G60 and then filtered through Celite. The clear dark solution of the sodium salt is added with stirring to 400 mL 6 N hydrochloric acid. The title compound separates as a yellow solid. The yield of crude product is 67.7 g. (93.8%). Recrystallization of this material from tetrahydrofuran-toluene (with decolorization with Darco G60) gives a yield of 40.2 g. (55.7%) of off-white crystals having a melting point of 210° C. dec. (uncorr.)

Analysis for: $C_{17}H_{12}O_2$: Calculated: C, 82.24; H, 4.87; Found: C, 81.96; H, 4.91

EXAMPLE 2

2-(5H-Dibenzo[a,d]cyclohepten-5-ylidene)propionic acid

5H-Dibenzo[a,d]cyclohepten-5-one is reacted with triethyl 2-phosphonopropionate in a manner similar to Example 1, to yield the title compound, m.p. 235°–236° C. (uncorr.)

Analysis for: $C_{18}H_{14}O_2$: Calculated: C, 82.42; H, 5.38; Found: C, 82.33; H, 5.77

EXAMPLE 3

Ethyl(5H-dibenzo[a,d]cyclohepten-5-ylidene acetate

A solution of triethyl phosphonoacetate (44.838 g., 0.200 mole) in dry dimethyl sulfoxide (100 mL.) is added rapidly with stirring to a solution of potassium-t-butoxide (23.005 g., 0.205 mole) in dry dimethyl sulfoxide (400 mL.) in a nitrogen atmosphere. The internal temperature rises from 23° C. to 33° C. After stirring for one-half hour at ambient temperature, 5H-dibenzo[a,d]cyclohepten-5-one (41.248 g., 0.200 mole) is added in a single portion. The resulting, deep wine-red solution is heated with stirring at 100±1° C. for twenty-two hours. The solvent is distilled in vacuo and the residue diluted with water. The resulting mixture is extracted with methylene chloride (1×250 ml., 3×100 mL). The combined extracts are successively washed with water (2×100 mL), saturated salt solution (1×100 mL), filtered through anhydrous sodium sulfate, then concentrated in vacuo to give an oil which solidifies on storage at room temperature. The yield of tan crystals melting at 61°–66° C. (uncorr.) is 50.4 g. (91.1%).

A portion (20.08 g.) of this material is recrystallized (uncorr.) in a yield of 13.80 g. (69.0%). An additional crystallization from methylene chloride-pentane affords colorless prisms melting at 72.5°–73.5° C. (uncorr.).

Analysis for: $C_{19}H_{16}O_2$: Calculated: C, 82.58; H, 5.84; O, 11.58; Found: C, 82.54; H, 5.85

EXAMPLE 4

Methyl(5H-dibenzo[a,d]cyclohepten-5-ylidene)acetate

Oxalyl chloride (2.665 g., 1.79 mL, 0.021 mole) is added to a suspension of (5H dibenzo[a,d]cyclohepten-5-ylidene)acetic acid (5.000 g., 0.020 mole) in dry benzene (70 mL). An exothermic reaction occurs and the solid gradually dissolves. After solution is complete, the mixture is refluxed for one hour, then concentrated in vacuo to give an amber oil which crystallizes on storage at ambient temperature. Absolute methanol (75 mL) is added to the solid acid chloride. The mixture is stirred magnetically until complete solution is obtained, then refluxed for 45 minutes. The solvent is evaporated in vacuo to give a crystalline solid. The yield of crude ester melting at 83.5°–84.5° C. (uncorr.) is 5.210 g. (99.31%). Recrystallization of this material from methanol affords colorless rods melting at 86.0°–86.5° C. (uncorr.) in a yield of 3.508 g. (66.86%).

Analysis for: $C_{18}H_{14}O_2$: Calculated: C, 82.42; H, 5.38; O, 12.20; Found: C, 82.43; H, 5.37

Using this general procedure, other esters (e.g.) n-propyl, isobutyl etc. may be prepared.

EXAMPLE 5

The ability of the compounds of the invention to modulate cell-mediated and humoral immune responses to specific antigens is determined in the murine methylated bovine serum albumin (MBSA) assay, in which MBSA is used to induce delayed hypersensitivity in mice.

The assay is carried out in the following manner

Groups of 8–10 male C57B1/6 mice (8 weeks old) obtained from Charles River are sensitized using a subcutaneous injection into the abdominal area of 0.1 ml of a 0.25% (normal) or 0.0025% (subliminal) emulsion of MBSA in Freund's complete adjuvant (day 0). Seven days after sensitization, the right hind paw is challenged subcutaneously with MBSA (0.05% in 0.05 ml of 0.9% saline) while the left hind paw receives 0.9% saline alone. Twenty-four hours after MBSA challenge, the hind paw volumes are measured by mercury plethysmography. MBSA-induced edema is measured as the difference between the left and right paw volumes. Drugs or drug vehicle (methylcellulose) are administered orally in a volume of 0.5 ml either 1 day prior to sensitization, on day 2 after sensitization, 1 hr prior to MBSA challenge, or 6 hr after challenge. The % change from control animals is recorded and analyzed statistically (unpaired, Student's t-test).

The following compounds were tested in the above procedure: (5H-dibenzo[a,d]cyclohepten-5-ylidene)acetic acid (DCHA), levamisole, aspirin and indomethacin. In subliminally sensitized mice, DCHA (0.1–100 mg/kg) showed a dose related stimulation (nonsignificant) of delayed hypersensitivity at 1 hr prior to antigen challenge. Levamisole significantly augmented the response only at 1 mg/kg, and no dose related effect was seen. Indomethacin and aspirin failed to stimulate the response, and indomethacin inhibited the response by 35% at 0.33 mg/kg. In normally sensitized mice, using similar doses, DCHA and levamisole (1 mg/kg, −1 hr regimen) stimulated the delayed response, but in this case, the DCHA augmentation was not dose related. Indomethacin and aspirin show inhibition of all doses tested. In other regimens, DCHA, at 10 and 100 mg/kg, showed stimulation of the delayed response both at 1 day before sensitization and at 2 days after sensitization in mice subliminally sensitized, the stimulation at the 10 mg/kg dose being significant in both regimens. In contrast, indomethacin showed insignificant stimulation only at 9 mg/kg when administered 1 day prior sensitization. DCHA and indomethacin were inhibitory at all doses when administered 6 hours after challenge in subliminally sensitized mice.

These results show that DCHA acts in a manner similar to levamisole, a well-known immunostimulant, in an assay measuring the effect of drugs on cell mediated immune responses. The well-known non-steroidal anti-inflammatory drugs aspirin and indomethacin either failed to show any stimulation of the cell mediated immunity or actually inhibited this response. Accordingly, in addition to its anti-inflammatory activity, DCHA possesses a significant stimulatory effect on the cell-mediated immunity, while levamisole is devoid of anti-inflammatory activity, and aspirin and indomethacin fail to show any stimulatory effect on the cell-mediated immunity.

EXAMPLE 6

In the tuberculin induced delayed hypersensitivity in guinea pigs test, the same effects are measured as in the MBSA procedure of Example 5, but a different animal model is involved.

According to this procedure, groups of male Hartley guinea pigs (Charles River) weighing 350–400 g. are used. Animals are sensitized with 0.4 ml of an emulsion consisting of 1 part IFA (Difco) to 1 part antigen (M. tuberculosis H37 Ra in 0.9% saline, Difco Labs.) with different amounts of antigen (2–200 $\mu$g). This is injected into four different sites, namely both front paws (subcutaneously) and hips (intramuscularly). Seven days later, drugs are administered per orally suspended or dissolved in 0.5% methylcellulose, 1 hour before challenge. The antigen challenge consists of 1000 units of purified protein derivative (PPD, Park Davis) injected in 0.1 ml of 0.9% saline into the right hind paw. Paw volume measurements in ml are made using mercury plethysmography at zero time (prior to challenge), and at 24 and 48 hours later. Percent changes from controls are calculated, and the unpaired Student's t-test is used to determine statistical significance.

In this test, DCHA (at 10 and 100 mg/kg) significantly increased the delayed hypersensitivity response at 24 hours in subliminally sensitized guinea pigs with small control foot pad volumes (~0.1 mL) while it failed to influence the response in normally sensitized animals whose control edema after challenge is >0.35 mL. Levamisole (at 10 and 100 mg/kg) showed a more variable pattern of activity, with stimulation of delayed hypersensitivity at 10 mg/kg when the control edema was approximately 0.2 mL and inhibition when the control edema was about 0.35 mL.

These results accord closely with the effects on the cell mediated immunity which are recorded for DCHA and levamisole in the MBSA assay of Example 5.

EXAMPLE 7

The effect of the compounds, used in the invention, on the humoral immunity is measured in the murine Jerne plaque assay.

The procedure is carried out as follows:

One day 0 of the assay, groups of 6 male C57B1/6 mice (Charles River; 8 weeks old) are injected intraperitoneally with a 2% suspension of sheep red blood cells (SRBC; $1 \times 10^8$ cells) in 0.5 ml of 0.9% saline. Drugs or drug vehicle are administered orally using single (day −1, 0, 2 or 3) or multiple day (days 0 to 3) regimens. Spleens are removed on day 4, weighed, viability determined (trypan blue exclusion) and the number of direct plaque-forming cells (PFC) is counted by the method of Cunningham, [*Immunology*, 14, 599–601, (1968)]. On day 4 sera from mice (treated day 1) are assayed for antibody to SRBC using a microtiter hemagglutination technique. Drug induced changes are expressed as a % change from control, and the data are analyzed using the unpaired Student's t-test.

DCHA (1–100 mg/kg, per orally) was tested at both single and multiple dose regimens in this assay. When administered on day 1 after sensitization, DCHA significantly inhibited the formation of plaque forming cells at 1 mg/kg (31%) and 100 mg/kg (58%). Also, DCHA reduced plaque cells significantly by 25% when administered on day 3. No significant response was noted when administered on day 0, day 2 or days 0–3. In mice receiving DCHA on day 1, there was no change from control in serum antibody titers to sheep red blood cells on day 4.

These results show that compounds such as DCHA inhibit antibody production but do not affect serum anti-sheep red blood cell antibody titers. This suggests that these compounds act to inhibit the humoral immunity, at least having an effect on the spleen, although the effect on other lymphoid tissues is not clear. It should be noted that Webb and Osheroff [*Proceedings of the National cademy of Sciences*, 73, 1300–1304 (1976)] have shown that humoral immunity was augmented in mice treated with indomethacin at the time of antigen sensitization. This effect has been attributed to the removal of $PGE_2$, the primary arachidonic acid metabolite that regulates humoral and cell mediated immunity. Therefore, while compounds such as DCHA exhibit true immunomodifying properties, the NSAIDs, such as indomethacin are known to affect both cellular and humoral immune responses in animals by reducing prostaglandin levels.

EXAMPLE 8

The effects of the compounds used in the invention on autoimmune responses is measured in the experimental allergic encephalomyelitis (EAE) test. This procedure measures the ability of drugs to inhibit the autoimmune response (T-cell mediated) and provides a basis for predicting activity against such neurological autoimmune-inspired disorders as multiple sclerosis.

The procedure is carried out as follows.

Groups of 10 male Lewis rats (Charles River; 170–190 g) are injected subcutaneously into the right hind paw with 0.1 ml of an emulsion containing 200 mg isologous spinal cord and *Mycobacterium tuberculosis* (2 mg/ml). Drugs are administered orally in 0.5% methylcellulose either daily beginning on the day of injection of the emulsion (day 0) until day 14, excluding weekends, or periodically on days −2, −1 and 0. Ascending motor paralysis appears on day 10. Quantitation of paralysis is evaluated between days 11 and 14 and the highest score obtained during this interval is used to calculate drug effects using the unpaired Student's t-test. The scoring system used is as follows: 0-no signs; 1-loss of >20 g body weight and lack of grooming; 2-tail flop; 3-hind paw paralysis; 4-forepaw and hind paw paralysis; and 5-moribund state or death.

DCHA and dexamethasone (a steroidal anti-inflammatory drug) were administered orally on days 0–14, they results in Table 1 were obtained.

dose of indomethacin was toxic (5/6 animals died of perforated intestinal ulcers by day 7 after antigen).

Thus, compounds such as DCHA have a significant activity in inhibiting the autoimmune response in the EAE autoimmune disease model.

EXAMPLE 9

The mitogen activated murine T and B lymphocyte proliferation test is used to determine the effects of immunomodulatory agents on the proliferation of murine T and B cell populations. The test is run to determine whether test compounds will enhance or depress the proliferation of T cells, whose proliferation has been initially stimulated by a mitogen, such as Concanavalin A (Con A); and enhance or depress the proliferation of B cells, whose proliferation has been stimulated by lipopolysaccharide (LPS).

The test procedure is as follows.

T lymphocytes are isolated from spleens of male CBA/J or NZB mice. Cell homogenates are prepared in Hank's balanced salt solution (HBSS). After removal of larger particles and repeated washing of the cells in

TABLE 1

| Treatment | Oral Dose[b] mg/kg | Δ Body Wt. (g) Day 0-14 Mean ± S.E. | Paralysis Score[a] Day 11-14 Mean ± S.E. | % Change from Control | Incidence of Paralysis |
|---|---|---|---|---|---|
| Normal | — | 105 ± 10 | — | — | — |
| Control (EAE) | — | 32 ± 9 | 2.1 ± 0.4 | — | 9/10 |
| DCHA | 10 | 11 ± 3 | 2.1 ± 0.2 | 0 | 10/10 |
|  | 30 | 18 ± 3 | 2.1 ± 0.1 | 0 | 10/10 |
|  | 90 | 41 ± 6 | 1.4 ± 0.3 | −33 | 7/10 |
| Dexamethasone | 0.1 | 19 ± 8 | 0.9 ± 0.3 | −57* | 5/10 |

[a]Highest score observed during the four days.
[b]10 rats in each dosing group.
*$P \leq 0.05$ These results show that DCHA (90 mg/kg) produced a non-significant reduction in paralysis, and that the animals showed less weight loss than EAE controls; dexamethasone significantly inhibited the paralysis, but this treatment produced a greater weight loss than control.

When DCHA, levamisole and indomethacin are administered on days −2, −1 and 0 prior to antigen, the results in Table 2 were obtained.

HBSS they are suspended in minimum essential medium (MEM) and passed through a glass wool column to remove macrophages. The cells are then incubated on a nylon wool column at 37° C. 95% air, 5% $CO_2$, for 45 minutes. The non-adherent T lymphocytes are then eluted from the column, counted, and adjusted to $20 \times 10^6$ cells/ml. 50 μl of cells are cultured (37° C., 95% air, 5% $CO_2$) cells/ml. 50 μl of cells are cultured

TABLE 2

| Treatment | Oral Dose[c] mg/kg | Δ Body Wt. (g) Day 0-14 Mean ± S.E. | Paralysis Score[a] Day 11-14 Mean ± S.E. | % Change from Control | Incidence of Paralysis | Deaths |
|---|---|---|---|---|---|---|
| Control | — | 21 ± 7 | 3.8 ± 1.7 | — | 6/6 | 0/6 |
| DCHA | 1 | 22 ± 5 | 3.0 ± 0.3 | −21 | 10/10 | 0/10 |
|  | 10 | 4 ± 8 | 2.3 ± 0.4 | −39** | 9/10 | 0/10 |
|  | 100 | 1 ± 4 | 1.7 ± 0.3 | −55** | 8/10 | 0/10 |
| Levamisole | 1 | 2 ± 4 | 3.3 ± 0.4 | −13 | 10/10 | 1/10 |
|  | 10 | 4 ± 6 | 2.6 ± 0.4 | −32 | 10/10 | 2/10 |
|  | 100 | 11 ± 6 | 1.9 ± 0.5 | −50* | 7/10 | 1/10 |
| Indomethacin | 1 | 10 ± 5 | 2.1 ± 0.2 | −45*** | 10/10 | 0/10 |
|  | 3 | 1 ± 7 | 3.2 ± 0.4 | −16 | 10/10 | 1/10 |
|  | 9 | — | — | — | — | 5/6[b] |

[a]Highest score observed during the four days
[b]Toxicity - all animals died before Day 7
[c]6–10 rats in each dosing group
*$P \leq 0.05$
**$P \leq 0.01$
***$P \leq 0.001$ These results show that when administered on days −2, −1 and 0 prior to antigen, DCHA (1–100 mg/kg) significantly inhibited paralysis score in a dose related manner. Levamisole (1–100 mg/kg, per orally) showed simular results, while indomethacin inhibited paralysis to a significant extent only at 1 mg/kg. The 9 mg/kg (37° C., 95% air, 5% $CO_2$) with compound, or compound and mitogen (0.025, 0.04 or 0.05 μg/culture of Concanavalin A) for 48 hours before the addition of 0.5 μCi of $^3$H-thymidine for the last 16 hours of culture.

The total volume of the culture system is 200 µl. The cells are then harvested on a multiple automatic sample harvester (Mash II), the glass fiber filter disks placed in 10 ml of xylene base scintillation fluid, and counted for 1 minute in a liquid scintillation counter. The results are expressed as CPM±SE. Comparisons are made between counts obtained with control cultures and cultures containing compound alone, or compound and concanavalin A.

In order to determine if active T lymphocyte stimulating agents have an effect on B lymphocyte proliferation, a mitogenic assay system is used in which the B cell mitogen lipopolysaccharide (LPS) is used in the culture system. Since T cells are required in the test system for B cells to proliferate, even with a B cell mitogen, enriched T cells are used for these cultures, in which the optimum distribution of cells for this assay of 90% T cells and 10% B cells is maintained. The concentration of LPS used with the compounds in these cultures is 1 µg/culture (near optimal), so that the effects of these compounds on B Cell proliferation can be clearly documented.

The results of the above T and B cell assays for the compound DCHA are given in Table 3.

immunomodulatory agent of significant activity, demonstrating a pronounced effect on cellular and humoral immunity response which is very similar to that exhibited by the well-known immunostimulant, levamisole. These attributes make this compound and its analogues useful not only in treating immunologically induced inflammatory connective tissue diseases such as rheumatoid arthritis and systemic lupus erythematosus, but other autoimmune associated disorders such as multiple sclerosis and hemolytic anemia, as well as diseases, whose etiology and/or progress is linked to T-cell and T- and B-cell function, such as neoplastic and metastatic diseases. This immunomodulatory activity is in marked contrast to the profile of activity of such conventional anti-inflammatory drugs as aspirin and indomethacin, which are devoid of any direct immunomodulatory activity, and which effect cellular and humoral immune responses only by reducing prostaglandin levels.

What is claimed is:

1. A method of modulating the immune response in mammals in need of modulation of the immune response which comprises administering thereto an amount effective to bring about said modulation of the immune response of a compound having the formula:

TABLE 3

| Compound | Compound Concentration µg/culture | 0.025 | CPM ± SE Concanavalin A concentration µg/culture | | CPM ± SE Lipopolysaccharide concentration µg/culture |
|---|---|---|---|---|---|
| | | | 0.04 | 0.05 | 1.0 |
| DCHA | 0 | 3804 ± 429 | | | |
| | 0.01 | *7903 ± 770 | | | |
| | 0.1 | 6563 ± 363 | | | |
| | 1.0 | *8538 ± 1416 | | | |
| DCHA | 0 | | 13,643 ± 716 | 19,296 ± 1042 | |
| | 0.05 | | 20,214 ± 1261 | *32,141 ± 3059 | |
| | 0.1 | | 19,873 ± 1196 | *29,866 ± 711 | |
| | 1.0 | | 14,415 ± 392 | 18,126 ± 1392 | |
| | 2.0 | | 12,857 ± 650 | 22,465 ± 2162 | |
| | 3.0 | | *9,560 ± 1121 | *13,011 ± 674 | |
| DCHA | 0 | | | | 29,978 ± 3956 |
| | 0.001 | | | | *83,712 ± 1096 |
| | 0.01 | | | | *86,725 ± 3824 |
| | 0.1 | | | | *81,010 ± 6486 |
| | 1.0 | | | | *71,382 ± 5170 |

*p < 0.05

These results show that at a suboptimal concentration of Concanavalin A (0.025 µg/culture), DCHA stimulates T-cell proliferation at the levels of 0.01, 0.1 and 1.0 µg/culture. Likewise, in the presence of 1 µg/culture of lipopolysaccharide, DCHA stimulates B-cell proliferation at 0.001, 0.01, 0.1 and 1 µg/culture. When tested in the presence of 0.04 and 0.05 µg/culture of Concanavalin A, DCHA showed T-cell proliferation at 0.05, 0.1 and 1.0 µg/culture, and at 0.05, 0.1 and 2 µg/culture, respectively. However, at 0.04 and 0.05 µg/culture of Concanavalin A, DCHA inhibits T-cell proliferation at 2 and 3 µg/culture, and at 1 and 3 µg/culture, respectively. These results show a dose responsive stimulation of cell proliferation and an upper dose level inhibition of T-cell proliferation which is characteristic of many immunomodifiers.

The experimental and test assay results show that (5H-dibenzo[a,d]cyclohepten-5-ylidene)acetic acid, a significant non-steroidal anti-inflammatory agent, is an

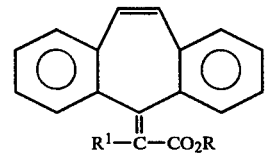

where R is hydrogen or an alkyl group of 1–4 carbon atoms, $R^1$ is hydrogen or an alkyl group of 1–4 carbon atoms, and pharmaceutically acceptable salts thereof.

2. The method of claim 1 wherein R and $R^1$ are both hydrogen.

3. The method of claim 1, wherein R is ethyl and $R^1$ is hydrogen.

4. The method of claim 1, wherein R is hydrogen and $R^1$ is methyl.

* * * * *